United States Patent
Vitello

(10) Patent No.: US 11,779,520 B1
(45) Date of Patent: Oct. 10, 2023

(54) CLOSURE FOR A MEDICAL DISPENSER INCLUDING A ONE-PIECE TIP CAP

(71) Applicant: Patrick Vitello, Pompano Beach, FL (US)

(72) Inventor: Patrick Vitello, Pompano Beach, FL (US)

( * ) Notice: Subject to any disclaimer, the term of this patent is extended or adjusted under 35 U.S.C. 154(b) by 833 days.

(21) Appl. No.: 16/459,971

(22) Filed: Jul. 2, 2019

Related U.S. Application Data

(60) Provisional application No. 62/693,202, filed on Jul. 2, 2018.

(51) Int. Cl.
| | |
|---|---|
| *A61J 1/14* | (2023.01) |
| *A61M 39/20* | (2006.01) |
| *A61M 5/50* | (2006.01) |
| *A61M 5/31* | (2006.01) |
| *B65B 7/28* | (2006.01) |

(52) U.S. Cl.
CPC ............ *A61J 1/1418* (2015.05); *A61J 1/1481* (2015.05); *A61M 39/20* (2013.01); *A61M 5/5086* (2013.01); *A61M 2005/3104* (2013.01); *A61M 2005/312* (2013.01); *B65B 7/2835* (2013.01)

(58) Field of Classification Search
CPC ....... A61J 1/1418; A61J 1/1481; A61M 39/20; A61M 5/5086; A61M 2005/3104; A61M 2005/312; B65B 7/2835
See application file for complete search history.

(56) References Cited

U.S. PATENT DOCUMENTS

| | | | |
|---|---|---|---|
| 722,943 | A | 3/1903 | Chappell |
| 732,662 | A | 6/1903 | Smith |
| 1,678,991 | A | 7/1928 | Marschalek |
| 1,970,631 | A | 8/1934 | Sherman |
| 2,477,598 | A | 8/1949 | Hain |
| 2,739,590 | A | 3/1956 | Yochem |
| 2,823,674 | A | 2/1958 | Yochem |
| 2,834,346 | A | 5/1958 | Adams |
| 2,875,761 | A | 3/1959 | Helmer et al. |
| 2,888,015 | A | 5/1959 | Hunt |
| 2,952,255 | A | 9/1960 | Hein, Jr. |
| 3,122,280 | A | 2/1964 | Goda |
| 3,245,567 | A | 4/1966 | Knight |

(Continued)

FOREIGN PATENT DOCUMENTS

| | | |
|---|---|---|
| DE | 202008018507 U1 | 2/2015 |
| EP | 0148116 A | 7/1985 |

(Continued)

OTHER PUBLICATIONS

Arai Tsugio, Pilfering Proof Cap, Jan. 1, 1996.

*Primary Examiner* — Laura A Bouchelle
*Assistant Examiner* — John A Doubrava
(74) *Attorney, Agent, or Firm* — Malloy & Malloy, PL; Jennie S. Malloy; Peter A. Matos

(57) ABSTRACT

A closure assembly for a medical dispenser which may include a one-piece tip cap having a flow restrictor and a removably connected sleeve disposed in surrounding relation to the flow restrictor. The tip cap further includes an access opening and an oppositely disposed closed end, wherein the flow restrictor is structured for a fluid sealing engagement with a discharge port of the medical dispenser, passing through said access opening. The closed end includes removably attached inner and outer end segments respectively formed on the flow restrictor and the sleeve and are collectively structured to define a removable connection between the flow restrictor and sleeve. A cover may be fixedly attached to the sleeve in overlying, covering relation to exterior surfaces of the inner and outer end segments.

12 Claims, 4 Drawing Sheets

(56) References Cited

U.S. PATENT DOCUMENTS

| | | |
|---|---|---|
| 3,323,798 A | 6/1967 | Miller |
| 3,364,890 A | 1/1968 | Andersen |
| 3,368,673 A | 2/1968 | Johnson |
| 3,489,268 A | 1/1970 | Meierhoefer |
| 3,574,306 A | 4/1971 | Alden |
| 3,598,120 A | 8/1971 | Mass |
| 3,610,241 A | 10/1971 | LeMarie |
| 3,674,181 A | 7/1972 | Marks et al. |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| 5,078,696 A | 1/1992 | Nedbaluk |
| D323,392 S | 1/1992 | Byrne |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Demark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,662,233 A * | 9/1997 | Reid .................... B65D 41/62 |
| | | 215/217 |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,842,567 A | 12/1998 | Rowe et al. |
| D402,766 S | 12/1998 | Smith et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| 6,126,640 A | 10/2000 | Tucker et al. |
| D431,864 S | 10/2000 | Jansen |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,235,376 B1 | 5/2001 | Miyazaki et al. |
| 6,279,746 B1 | 8/2001 | Hussaini et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. et al. |

(56) References Cited

U.S. PATENT DOCUMENTS

| | | |
|---|---|---|
| 6,682,798 B1 | 1/2004 | Kiraly |
| 6,726,652 B2 | 4/2004 | Eakins et al. |
| 6,726,672 B1 | 4/2004 | Hanly et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| 7,497,330 B2 | 3/2009 | Anthony et al. |
| 7,503,453 B2 | 3/2009 | Cronin et al. |
| D589,612 S | 3/2009 | Sudo |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| 7,641,636 B2 | 1/2010 | Moesli et al. |
| D608,900 S | 1/2010 | Giraud et al. |
| 7,681,606 B2 | 3/2010 | Khan et al. |
| D612,939 S | 3/2010 | Boone, III et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| 8,672,902 B2 | 3/2014 | Ruan et al. |
| D701,304 S | 3/2014 | Lair et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| 9,125,976 B2 | 9/2015 | Uber, III et al. |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| 9,336,669 B2 | 5/2016 | Bowden et al. |
| D756,777 S | 5/2016 | Berge et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| 9,687,249 B2 | 6/2017 | Hanlon et al. |
| D789,529 S | 6/2017 | Davis et al. |
| 9,744,304 B2 | 8/2017 | Swift et al. |
| 9,764,098 B2 | 9/2017 | Hund et al. |
| D797,928 S | 9/2017 | Davis et al. |
| D797,929 S | 9/2017 | Davis et al. |
| 9,821,152 B1 | 11/2017 | Vitello et al. |
| D806,241 S | 12/2017 | Swinney et al. |
| 9,855,191 B1 | 1/2018 | Vitello et al. |
| D807,503 S | 1/2018 | Davis et al. |
| D815,945 S | 4/2018 | Fischer |
| 9,987,438 B2 | 6/2018 | Stillson |
| D820,187 S | 6/2018 | Parker |
| 10,039,913 B2 | 8/2018 | Yeh et al. |
| D825,746 S | 8/2018 | Davis et al. |
| D831,201 S | 10/2018 | Holtz et al. |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B2 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 2001/0034506 A1 | 10/2001 | Hirschman et al. |

(56) References Cited

U.S. PATENT DOCUMENTS

| | | |
|---|---|---|
| 2001/0056258 A1 | 12/2001 | Evans et al. |
| 2002/0007147 A1 | 1/2002 | Capes et al. |
| 2002/0023409 A1 | 2/2002 | Py |
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0022685 A1 | 1/2003 | Nilsson |
| 2003/0146617 A1 | 8/2003 | Franko, Sr. et al. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer et al. |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0050351 A1 | 3/2010 | Colantonio et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182686 A1 | 7/2015 | Okihara |
| 2015/0191633 A1 | 7/2015 | De Boer et al. |
| 2015/0246185 A1* | 9/2015 | Heinz ................. A61M 5/3134 264/271.1 |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067144 A1 | 3/2016 | Chang |
| 2016/0067422 A1 | 3/2016 | Davis et al. |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0194121 A1 | 7/2016 | Ogawa et al. |
| 2016/0250420 A1 | 9/2016 | Maritan et al. |
| 2016/0279032 A1 | 9/2016 | Davis et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0297781 A1 | 10/2017 | Kawamura |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2019/0308006 A1 | 10/2019 | Erekovcanski et al. |
| 2019/0388626 A1* | 12/2019 | Okihara ................. A61M 5/50 |
| 2022/0008645 A1 | 1/2022 | Ukai et al. |

FOREIGN PATENT DOCUMENTS

| | | |
|---|---|---|
| GB | 486367 A | 6/1938 |
| JP | H08002544 A | 1/1996 |
| KR | 101159987 B1 | 6/2012 |
| WO | 2008000279 A1 | 1/2008 |
| WO | 2017086607 A | 5/2017 |

* cited by examiner

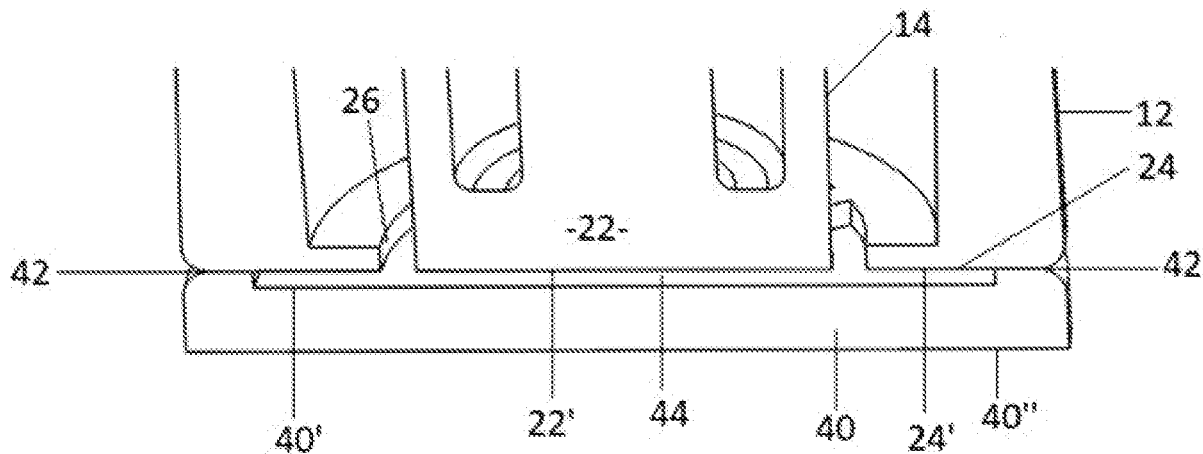
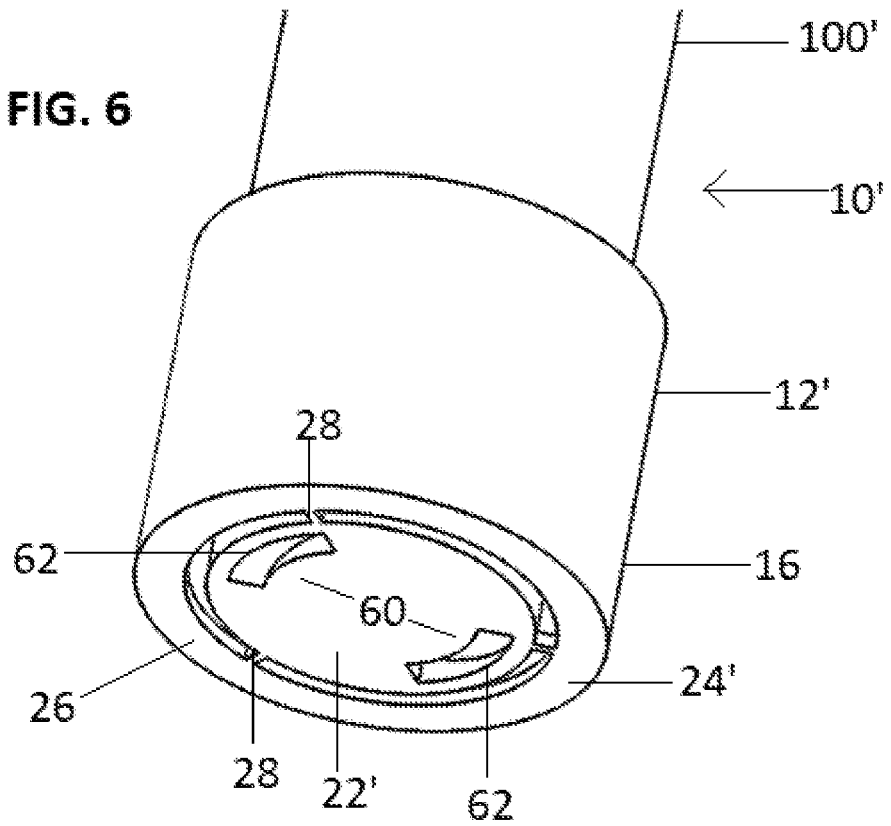

CLOSURE FOR A MEDICAL DISPENSER INCLUDING A ONE-PIECE TIP CAP

BACKGROUND OF THE INVENTION

CLAIM OF PRIORITY

The present application is based on and a claim of priority is made under 35 U.S.C. Section 119(e) to a provisional patent application that is currently pending in the U.S. Pat. and Trademark Office, namely, that having Serial No. 62/693,202 and a filing date of Jul. 2, 2018, and which is incorporated herein by reference.

FIELD OF THE INVENTION

The present invention is directed to a closure assembly for a medical dispenser including a one-piece tip cap. A closed end of the tip cap includes removably attached inner and outer end segments, respectively formed on the flow restrictor and the sleeve, and structured to define a removable connection between the flow restrictor and sleeve.

DESCRIPTION OF THE RELATED ART

In the medical field, it is a common procedure for authorized medical personnel to order medicine or other substances to be administered to a patient whether orally, by an injection or intravenously through an IV. It is also a relatively common procedure for a number of administering devices, such as a syringe, to be pre-filled by authorized personnel whether within the hospital or at another filling station. However, such a filling station is typically located in a remote part of the facility, relative to the patient care area, where the medicine is to be administered. Because of the remote location of many nurse's stations, relative to a filling station, a fluid or drug loaded syringe or other medical device is frequently given to another person for delivery to a nurse's station for subsequent dosing of the patient. In the case where a prefilled drug in the syringe is very expensive or addictive, such as but not limited to, morphine, there is a danger of tampering, by a person seeking unauthorized access to the prefilled contents of the syringe or medical device.

If tampering does occur, the potential for serious consequences exists. For example, there is a possibility that the prescribed medicine will be replaced by some other, unauthorized substance. As an illustration of this, if saline solution were substituted for a dose of morphine or other medication, the result could be extremely serious. Thus, there is a problem of knowing if a sealed, pre-loaded syringe or other administering device has, or has not, been compromised by tampering and/or exposed to contamination so that it is no longer sterile.

In addition to the administration of drugs, medicine, etc., meaningful protection is required in the use of enteral feeding sets. As commonly recognized in the medical and related professions, the term "enteral" relates to the administration or removal of fluid to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are used in the treatment of numerous medical conditions. Different types of connectors, such as a "female" connector may be attached to the discharge end or discharge port of an IV bag or like medical device/container. Such an appropriate female connector may be in the form of a female luer connector which at least partially defines, along with a male luer connector, a "luer lock" connector assembly, as is well known in the medical profession. In periods of non-use, it is important to maintain such connectors associated with an IV facility, in a closed and fluid sealed condition in order to maintain sterility and integrity of the IV fluid prior to use.

Therefore, regardless of the known or conventional attempts to provide a fluid restricting closure to protect the contents of preloaded medical dispensers or administering devices including enteral devices, certain problems still remain in this field of art. Accordingly, there is a need in this area for an improved, closure assembly which provides a secure and reliable fluid restricting or fluid sealing connection to the discharge port, fixture or connector of a medical dispenser of the type set forth herein. If any such improved closure assembly were developed, it would preferably also overcome known disadvantages in the production and/or assembly of conventional closures, while also including tamper evident characteristics. In doing so, if any such closure assembly were developed it would be advantageous to include tamper evident capabilities which provide evidence of authorized or unauthorized access to the discharge port of a syringe or other type of medical dispenser. In addition, if any such improved closure assembly were developed, it should help reduce, if not eliminate, the need for time-consuming, costly and overly complicated production techniques associated with the production of more conventional closures for medical devices by reducing the complexity of the manufacturing process, possibly down to a single molding process, packaging operation and sterilization process (if applicable).

Also, if any such closure assembly were developed, it should further be capable of use with little or no structural modification to a variety of different connectors, fixtures, administering devices, discharge ports, etc., while at the same time being structurally and operatively reliable, and with improved cost effectiveness relative to the manufacture and assembly thereof.

SUMMARY OF THE INVENTION

This invention is directed to a closure assembly for a medical dispenser, wherein at least one embodiment thereof may incorporate a one-piece, tamper evident tip cap. Accordingly, in the context of the present invention, the term "tamper evident" refers to the closure assembly and/or tip cap associated therewith, sealing and providing evidence of authorized or unauthorized access to the discharge port of a syringe or other type medical dispenser.

Moreover, the closure assembly of the present invention preferably comprises a tip cap having a one-piece construction, with a goal of helping to simplify the manufacturing process, possibly down to a single molding process, packaging operation and sterilization process (if applicable). Further, in the case of non-sterile configurations, the one-piece construction could further simplify the process in terms of feeding the parts directly into bulk packaging as they are removed from the molding machine, thereby requiring no secondary operations.

Additionally, in one preferred embodiment of the present invention, the closure assembly includes a one-piece tip cap having a flow restrictor, and a removably connected sleeve disposed in surrounding relation to the flow restrictor. When operatively disposed on a prefilled syringe or other medical dispenser, the flow restrictor is disposed in sealing engagement with the discharge port of the medical dispenser. It is recognized that the versatility of the closure assembly of the present invention facilitates its use with different medical dispensers. Accordingly, the term "discharge port" is meant to include the structure, section, segment or component of the medical dispenser through which the contents held in the dispenser exits. By way of non-limiting example, the discharge port of a prefilled, oral syringe will include a nozzle, a flow channel within the nozzle, and a terminal opening formed in the outer end of the nozzle through which the contents of the syringe pass upon exiting the interior thereof.

The flow restrictor further includes an access opening and a closed end disposed opposite to the access opening. As such, the discharge port of the medical dispenser to which the tip cap is connected passes into the interior of the sleeve and into sealing engagement with a sealing structure associated with the flow restrictor. Further by way of example, the sealing structure associated with the flow restrictor of at least one embodiment of the present invention may include an elongated sealing stem dimensioned and configured to pass into the interior of the discharge port, such as into the nozzle in sealing engagement within the interior flow path. The sealing stem and the interior of the discharge port may be cooperatively structured and dimensioned to establish a sealing frictional engagement therebetween.

By virtue of such a frictional engagement, the flow restrictor may be removed from the interior of the sleeve by exerting a pulling force on the sleeve, medical dispenser and/or both. As set forth in greater detail hereinafter, removable interconnection between the flow restrictor and the sleeve will result in a separation or disconnection therebetween when authorized or unauthorized access to the contents of the medical dispenser/syringe is attempted. As will also be more fully explained, securement of the discharge port to the flow restrictor is accomplished by exerting an installing "push-force" on the flow restrictor, independent of the installing push force being exerted on the sleeve.

More specifically, the closed end of the tip cap is structured to define an inner end segment, mounted on the flow restrictor, and an outer end segment, mounted on the sleeve. The inner end segment and the outer end segment respectively, of the flow restrictor and sleeve, are removably connected to one another. Removable connection of the flow restrictor to the sleeve comprises a frangible connection between the inner end segment and an outer end segment. As a result, a pulling force exerted on either or both the medical dispenser and closure assembly, when in sealing engagement, will result in a breakage of the frangible connection and a separation of the inner and outer end segments of the closed end. As a further result, the flow restrictor will be disconnected from the sleeve and allowed to pass outwardly there from while maintaining a sealed engagement with the discharge port of the medical dispenser.

In addition, the closed end of the tip cap preferably comprises a substantially flat exterior surface, which may be more specifically defined by the exterior surfaces of the inner and outer end segments being aligned in substantially coplanar relation to one another. As used herein, the term "coplanar" in regard to the alignment of the exterior surfaces of the inner and outer end segments is not meant to necessarily describe a precise coplanar alignment. Rather the term "coplanar" is meant to describe a planar alignment which defines the aforementioned substantially flat configuration of the exterior surface of the closed-end. As such, the flat exterior surface of the closed-end will allow the aforementioned push-force to be exerted by the medical dispenser, almost exclusively on the flow restrictor and not the sleeve, when the exterior surface of the closed end is disposed on a substantially flat or planar supporting surface. The separation of the flow restrictor, while still in a sealed engagement with the discharge port, will be evidence of tampering or attempted authorized access to the contents of the syringe/medical dispenser.

In order to prevent or restrict unauthorized tampering with the closure assembly, the tip cap may include a cover disposed in overlying, covering relation to the exterior closed end of the of the tip cap. The cover is preferably fixedly connected to the exterior surface of the outer end segment, in minimally spaced, non-connected relation to the exterior surface of the inner end segment of the flow restrictor. As a result, fluid sealing connection of the medical dispenser/discharge port to the flow restrictor will also be accomplished by a push-force being exerted on the medical dispenser as it enters the access opening of the tip cap. As indicated above, the installing push-force will be applied concurrent to the exterior surface of the cover being disposed on a flat supporting surface, as generally set forth above and explained in greater detail hereinafter.

Yet another embodiment of the present invention includes the structuring of the tip cap specifically including, but not limited to, the flow restrictor in a manner which facilitates the rotational attachment of the flow restrictor into the sealing engagement with the discharge port of the medical dispenser. In such an additional preferred embodiment, an attachment member is cooperatively structured with the tip cap to facilitate the rotary attachment. Further, the attachment member is independently structured and is originally not connected to or made a part of the tip cap.

Cooperatively structured sections of a ramp and cliff structure are disposed on both the exterior surface of the inner end segment of the flow restrictor and the interior surface of the attachment member. The disposition and structure of cooperative ramp and cliff sections results in the rotational force being exerted only on the flow restrictor as it is connected in sealing engagement with the discharge port. In contrast, the rotational force will not be exerted on the sleeve thereby preventing a breakage of the aforementioned frangible connection and an unintended separation or disconnection of the flow restrictor from the sleeve.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 5 is a detailed view in partial cutaway of the embodiment of FIGS. 3 and 4.

FIG. 6 is a perspective view in partial cutaway of yet another preferred embodiment of the closure assembly of the present invention.

Like reference numerals refer to like parts throughout the several views of the drawings.

DETAILED DESCRIPTION OF THE PREFERRED EMBODIMENT

Figure 1:
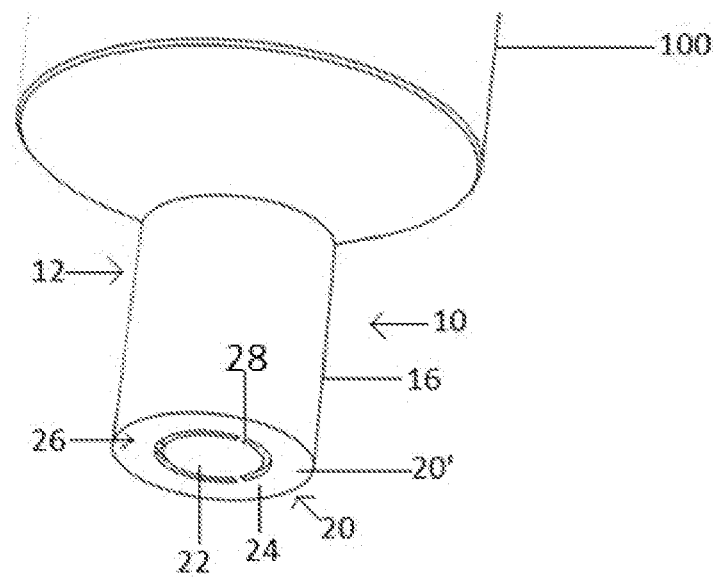
FIG. 1 is a perspective view in partial cutaway of one embodiment of the closure assembly of the present invention.
Figure 2:
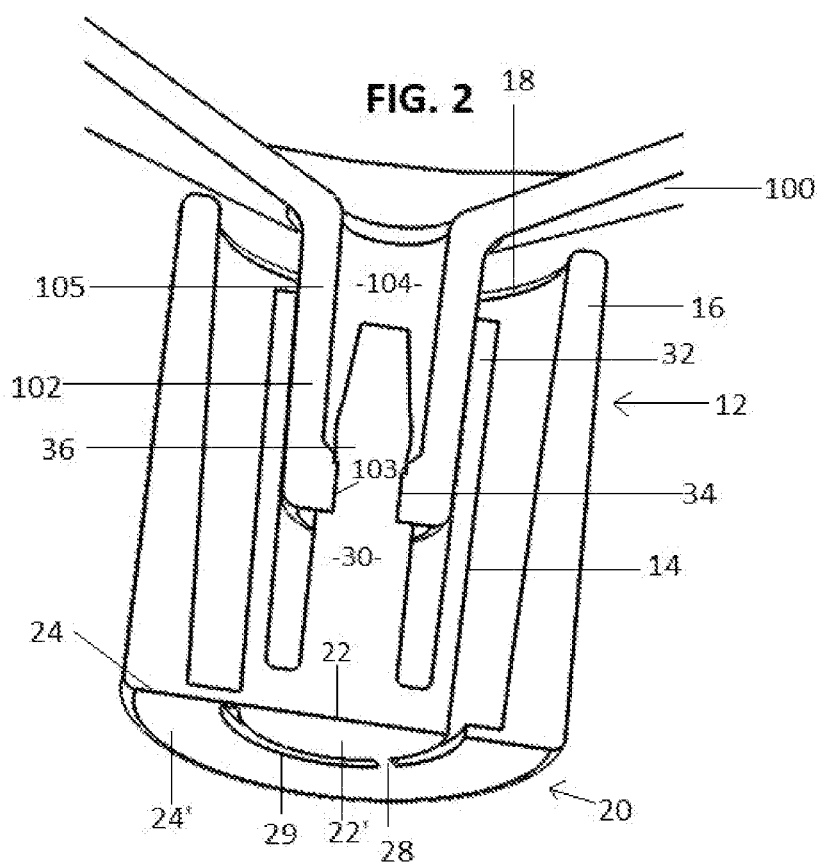
FIG. 2 is a sectional view in partial cutaway of the embodiment of FIG. 1.

As represented in the accompanying drawings, the present invention is directed to a closure assembly, generally indicated as 10, and with initial reference to FIGS. 1 and 2, in one preferred embodiment is represented as being attached to a medical dispenser 100. As explained herein, the medical dispenser 100 may comprise, but is not limited to, an oral prefilled syringe.

In more specific terms, the closure assembly 10 comprises a one-piece tip cap generally indicated as 12 including a flow restrictor 14 and an outer surrounding sleeve 16, removably attached to the flow restrictor 14. The tip cap 12 includes an access opening 18 at least partially defined by the open end of the sleeve 16. In addition, the closure assembly tip cap 12 includes a closed end generally indicated as 20 comprising an inner end segment 22, integrally or otherwise connected to the flow restrictor 14 and an outer end segment 24, integrally or otherwise fixedly connected to the sleeve 16.

The removable connection between the flow restrictor 14 and the sleeve 16 is accomplished preferably, but not necessarily, by a frangible connection generally indicated as 26. The frangible connection 26 comprises at least one, but preferably a plurality of frangible tabs 28 removably interconnecting the inner and outer end segments 22 and 24. Further, the plurality of frangible tabs 28 are disposed in spaced relation to one another about the outer and inner peripheries, respectively of the inner end segment 22 and the outer end segment 24.

As represented in FIG. 2, the tip cap 12 includes a substantially elongated sealing stem 30 disposed on the interior thereof in surrounded relation to skirt 32. The sealing stem 30 is cooperatively dimensioned and configured to establish a sealing engagement 34 with the discharge port 102. Such cooperative dimensioning, between the sealing stem 30 and the discharge port 102, facilitates sliding entry of the sealing stem 30 through the terminal opening 103 and into the interior of a flow channel 104 of the nozzle 105 of the discharge port 102. Further, the sealing stem 30 may include a bulbous or enlarged diameter portion 36, which forces an enlargement of the terminal opening 103 as the bulbous portion 36 passes there through, into the interior of the flow channel 104. Also, the bulbous portion 36 facilitates the establishment of a frictional, sealing connection 34, when an installing "push-force" is exerted on the flow restrictor 14. Also, the presence and dimension of bulbous portion 36 is such as to establish a sufficient resistance to separation of the discharge port 102 from the sealing stem 30. As a result, the exertion of a "pulling-force" on the medical dispenser 100, once attached to the sealing stem 30, is enough to break the frangible connection 26 and force a removal of the flow restrictor 14 from the interior of the sleeve 16.

The aforementioned installing "push-force" is exerted on the flow restrictor 14 by a forced movement of the medical dispenser 100, as the discharge port 102 passes through the access opening 18, into the interior of the closure assembly tip cap 12. The application of the aforementioned installing "push-force" will be described in greater detail hereinafter, as it applies to both the embodiments of the closure assembly 10 as respectively represented in FIGS. 1-2 and 3-5.

Additional features of the closed end 20 of the tip cap 12 include the exterior surface 20' having a substantially flat configuration, as represented. The flat configuration of the exterior surface of the closed end 20 is defined by the exterior surfaces 22' and 24' of the inner and outer end segments 22 and 24 also being flat and aligned in planar relation. Accordingly, the configuration of the flat exterior surface 20' may comprise and be defined by an aligned planar relation and/or substantially coplanar relation of the exterior surfaces 22' and 24' of the inner and outer end segments 22 and 24. It is emphasized, the term "coplanar" as used herein, in regard to the alignment of the exterior surfaces 22' and 24' is not necessarily meant to describe a precise coplanar alignment. Rather, the term "coplanar" as used herein is meant to describe a sufficient planar alignment between the exterior surfaces 22' and 24', to accomplish a concurrent disposition of both the exterior surfaces 22' and 24' in supported engagement on a flat supporting surface, such as 300, schematically represented in FIG. 4, and explained in greater detail hereinafter.

As set forth above, the flow restrictor 14 and the sleeve 16 are removably connected by virtue of the frangible connection 26 and the plurality of frangible tabs 28 serving to interconnect the inner end segment 22 and the outer end segment 24. When a plurality of the frangible tabs 28 are utilized, they are disposed in spaced relation to one another, as indicated, possibly resulting in a plurality of elongated apertures 29 disposed therebetween. However, the apertures 29 are sufficiently small to restrict or prevent the entrance of any tool, instrument, etc. to pass there-through in an attempt to access the contents of the medical dispenser 100 by defeating the sealing engagement 34 between the flow restrictor 14 and the discharge port 102.

Figure 3:
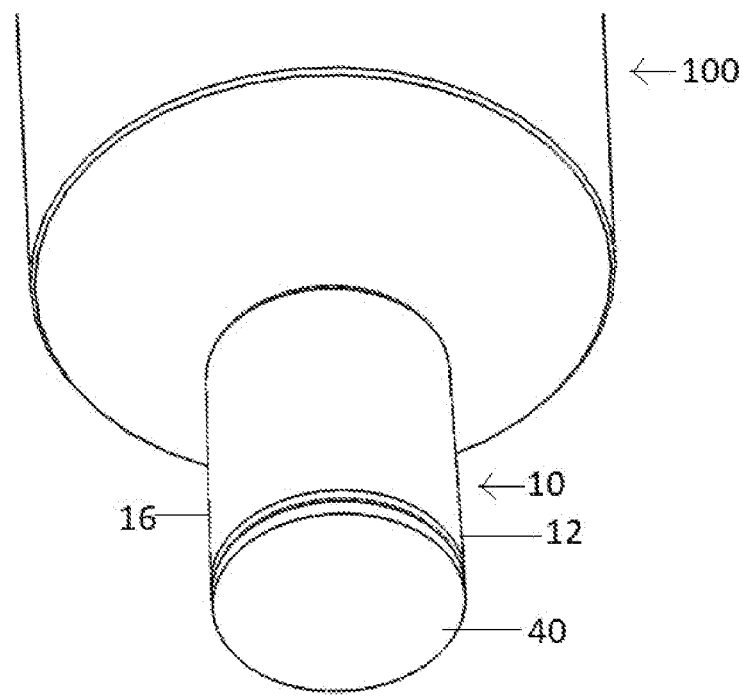
FIG. 3 is a perspective view in partial cutaway of another embodiment of the closure assembly of the present invention.
Figure 4:
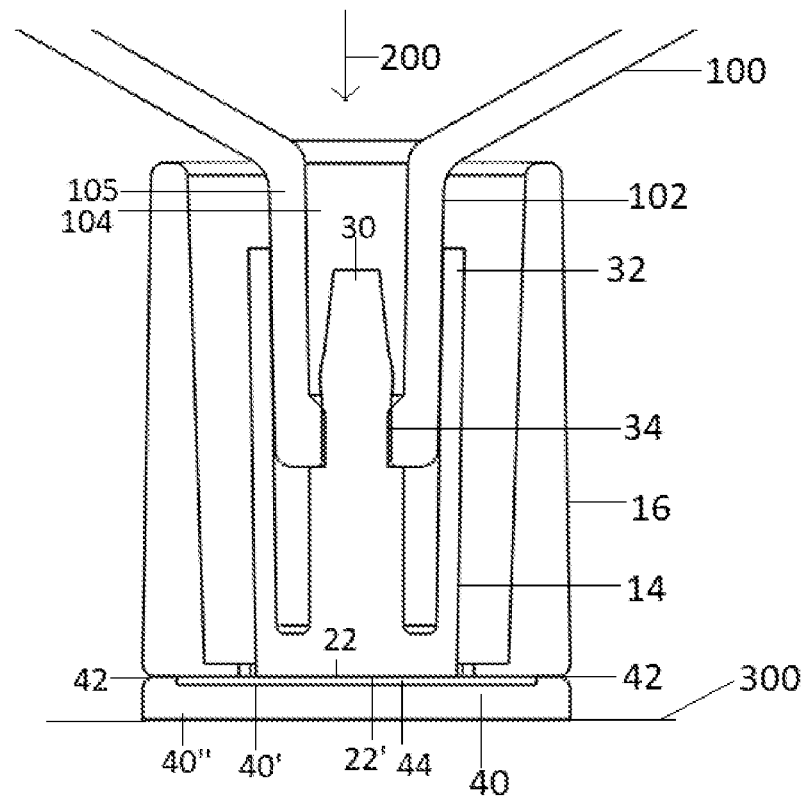
FIG. 4 is a sectional view in partial cutaway of the embodiment of the closure assembly as represented in FIG. 3.

With reference now to FIGS. 3-5, additional protective features of the tip cap 12 may include the provision of a cover 40 being disposed in covering, overlying relation to the flat exterior surface 20' of the closed end 20. In such a protective position, the cover 40 is also disposed in overlying, covering relation to the substantially coplanar exterior surfaces 22' and 24' of the inner and outer end segments 22 and 24. As clearly represented in FIGS. 4 and 5, the cover 40 is fixedly secured, as at 42, to the outer end segment 24 of sleeve 16, such as by welding. Further, the cover 40 includes an interior surface 40' which is disposed in spaced, non-engaging relation to the exterior surface 22' of the inner end 22 of the flow restrictor 14. As such, a minimally dimensioned space 44 exists between the exterior surface 22' of the inner end segment 22 of the flow restrictor 14 and the interior surface 40' of the cover 40. This spacing 44 prevents an inadvertent attachment or connection between the cover 40 and the inner end segment 22, when the cover 40 is welded or otherwise fixed, as at 42, to the exterior surface 24' of the outer end segment 24 of the sleeve 16.

As a result, the spacing 44 assures that the cover 40 is not inadvertently welded or attached directly to the flow restrictor 14, via the inner end segment 22, when the cover 40 is being welded to the exterior surface 24'. Also, the spacing 44 is minimally dimensioned to establish the distance between the inner surface 40' and the exterior surface 22' of the inner end segment 22 to be a preferred range of generally about 0.005 inches. This minimal distance (of generally about 0.005 inches) facilitates the establishment of the fluid sealing engagement between the discharge port 102 and the flow restrictor 22, utilizing the aforementioned inwardly or downwardly directed push-force.

As schematically represented in at least FIG. 4, the exterior surface 40'' of the cover 40, also includes a substantially flat or planar configuration. Accordingly, when the cover 40 is connected to the remainder of the tip cap 12 and the exterior surface 40'' is placed on a flat supporting surface 300, a downwardly directed, installing push-force may be exerted directly on the flow restrictor 14, as the nozzle 105 of the flow restrictor 102 passes into and through the access opening 18. Due to the minimal dimension (about 0.005 inches) of the spacing 44, the downwardly directed push-force 200 will result in a minimal displacement of the flow restrictor 14, such that the exterior surface 22' will be temporarily deformed or displaced into supported engagement with the interior surface 40' of the cover 40. Therefore, the minimal dimensioning of the space 44 and the temporary supported engagement of the exterior surface 22' with the interior surface 40 will not significantly displace the plurality of frangible tabs 28 or exert a sufficient force thereon to cause their breakage. As a result, the flow restrictor 14 and the sleeve 16 will remain interconnected by the frangible connection 26, during the application of the installing "push-force" on the flow restrictor 14.

With regard to the embodiment of FIGS. 1 and 2, a similar distribution of the installing push-force 200 will occur, absent the existence of the cover 40. Moreover, when the flat exterior surface 20' of the closed end 20 is disposed on a flat supporting surface, as at 300, both of the exterior surfaces 22' and 24' will be concurrently disposed in supported engagement with the supporting surface 300, due to their substantially coplanar alignment. Similar to the embodiment of FIG. 4, the application of the installing push-force 200 by the insertion of the discharge port 102 into the interior of the tip cap 12, will result in the push force 200 being primarily, if not exclusively, exerted on the flow restrictor 14. Concurrently, the exterior surface 22' of the inner end segment 22 thereof will be supported by the supporting surface 300. Therefore, the plurality of frangible tabs 28 will not be displaced or broken during the application of the push-force 200. In turn, the frangible connection 26 will remain intact and maintain the connection between the inner and outer end segments 22 and 24 of the flow restrictor 14 and the sleeve 16.

Figure 7:
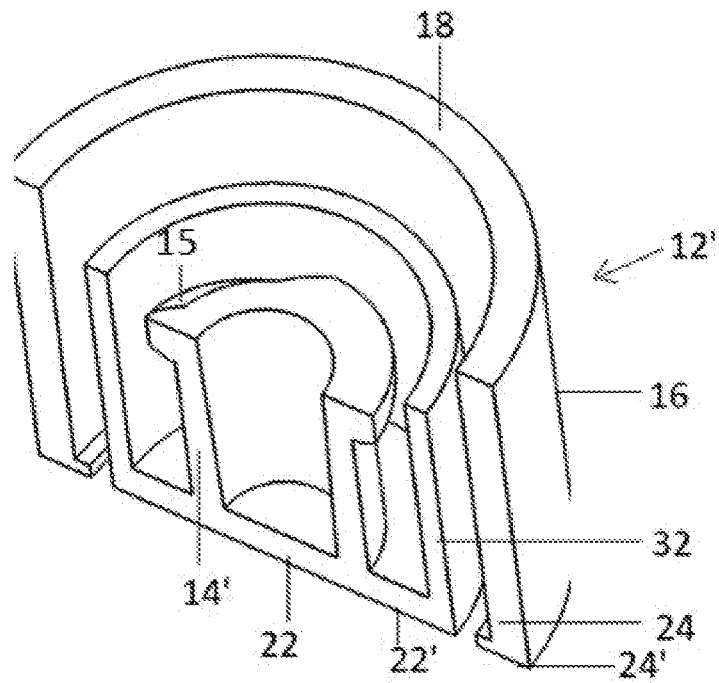
FIG. 7 is a sectional view in perspective of the embodiment of FIG. 6.
Figure 8:
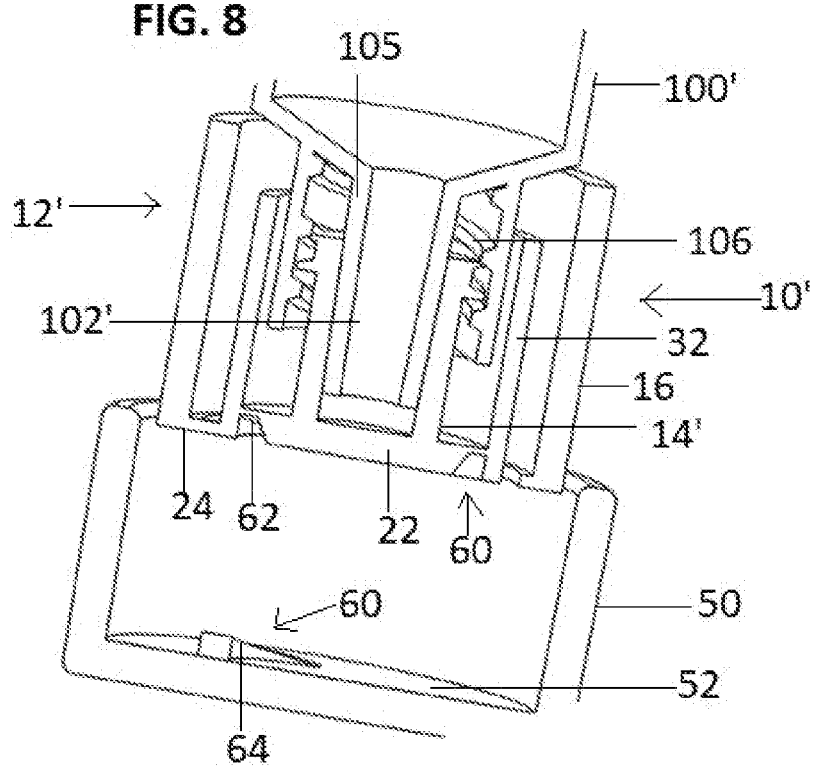
FIG. 8 is a sectional view of the embodiment of FIGS. 6 and 7 operatively disposed in sealing engagement with a medical dispenser.

As represented in FIGS. 6-8, yet another preferred embodiment of the present invention comprises the closure assembly 10' having similar structural and operative features to the embodiments of FIGS. 1-5. However, the closure assembly 10' differs somewhat structurally and operatively by being rotationally connected to the medical dispenser 100' rather than being connected thereto by the aforementioned push-force 200.

In more specific terms, the closure assembly 10' comprises a tip cap 12' including a flow restrictor 14' disposed within the interior of a sleeve 16. The flow restrictor 14' and the sleeve 16 are removably connected to one another by means of the frangible connection 26 serving to removably interconnect the inner end segment 22 and the outer end segment 24, in the manner described above. Also, a skirt 32 is disposed in substantially surrounding relation to the flow restrictor 14' and may serve to align the discharge port 102' with the flow restrictor 14'. The flow restrictor 14' differs in structure and function by being rotationally attached to the flow restrictor 102' of the medical dispenser 100'. This is accomplished through the provision of an external thread or rib structure 15 being secured to an outermost free end of the flow restrictor 14', disposed opposite to the inner end segment 22 thereof. As also represented, the thread or rib 15 is disposed, dimensioned and configured to rotationally engage the internal threaded surface 106 of the discharge port 102', which surrounds the nozzle 105 thereof and when so connected established a fluid sealing engagement between the flow restrictor 14' and the discharge port 102'.

As with the embodiments of FIGS. 1-5, an outward pulling force exerted on the medical dispenser 100', once it is connected to the flow restrictor 14', will result in a breakage of the frangible connection 26 and removal of the connected flow restrictor 14' and the discharge port 102' from the interior of the sleeve 16. However, as indicated the attachment of the flow restrictor 14' in fluid engaging relation to the discharge port 102' is accomplished by a rotational force being exerted on the closure assembly 10' and/or on the medical dispenser 100'.

Therefore, the embodiment of FIGS. 6-8 further includes the provision of an attachment member 50. The attachment member 50 is not initially connected to or structured as an integral or fixed component of the closure assembly 10'. Rather, the attachment member 50 is removably connected in at least partially surrounding, rotationally driving engagement with the exterior surface 22' and/or inner end segment 22 of the closed-end 20. The rotational, driving engagement therebetween is established, at least in part, by a ramp and cliff structure 60 including one or more first ramp and cliff sections 62 formed on and at least partially within the inner end segment 22 of the flow restrictor 14'. Further, the ramp and cliff structure 60 also includes at least one second ramp and cliff section 64 formed on the interior surface 52 of the attachment member 50. Upon engagement of the ramp and cliff sections 62 and 64 and due to the cooperative structuring thereof, a rotational driving force may be exerted on the tip cap 14' by a forced rotation of the attachment members 50 in a single installing (clockwise) direction.

It is to be noted that because the first ramp and cliff section 62 is formed on the inner end segment 22 of the flow restrictor 14' a rotational force applied by the attachment member 50 will only be exerted on the flow restrictor 14' and not the sleeve 16. As a result, no breakage or disconnecting force will be exerted on the frangible connection 26, resulting in the flow restrictor 14' and the sleeve 16 remaining in connected engagement with one another, while the rotational installing force is applied to the tip cap 12'.

Further, due to the cooperative structuring of the first and second ramp and cliff sections 62 and 64, rotation of the tip cap 12' in the opposite, rotational direction (counter-clockwise) will be prevented. As a result, the tip cap 12' cannot be unthreaded or rotationally disconnected from the discharge port 102' of the medical dispenser 100', utilizing the attachment member 50. Therefore, once the tip cap 12' is connected to the medical dispenser 100' by sealing engagement of the flow restrictor 14' with the flow restrictor 102', the tip cap 12' cannot be unthreaded or rotationally disconnected. Access to the contents of the medical dispenser 100' can only be obtained by exerting a pulling or rotational force on the exterior of the sleeve 16, while it remains attached to the flow restrictor 14'. Such pulling or rotational force will result in a breakage of the frangible connection 26 and a removal of the sleeve 16 from the flow restrictor 14' and thereby provide clear evidence of attempted tampering or authorized access.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical dispenser comprising:
a tip cap including a flow restrictor and a sleeve disposed in surrounding relation to said flow restrictor,
said flow restrictor operatively disposed in fluid sealing engagement with a discharge port of the medical dispenser,
said tip cap further including an access opening and an oppositely disposed closed end, said closed end comprising an exterior surface having a flat configuration,
a cover fixedly connected to said sleeve in overlying, covering relation to said exterior surface of said closed end,
said closed end further comprising an inner segment formed on said flow restrictor and an outer segment, formed on said sleeve, and
said inner and outer end segments removably attached to one another and collectively defining a removable connection of said flow restrictor to said sleeve.

2. The closure assembly as recited in claim 1 wherein said flat configuration is defined by exterior surfaces of said inner and outer end of segments disposed in substantially coplanar relation to one another.

3. The closure assembly as recited in claim 1 wherein said flow restrictor is cooperatively structured with the discharge port to establish said fluid sealing engagement by a push-force exerted on said flow restrictor, substantially independently of said push-force being exerted on said sleeve.

4. The closure assembly as recited in claim 1 wherein said cover is fixedly connected to an exterior surface of said outer end segment, in spaced relation to an exterior surface of said inner end segment.

5. The closure assembly as recited in claim 1 wherein said flow restrictor comprises a sealing stem operatively disposed in frictional engagement within the discharge port and in said fluid sealing engagement therewith.

6. The closure assembly as recited in claim 2 further comprising a frangible connection disposed in removably connecting relation between said inner end segment and said outer end segment.

7. The closure assembly as recited in claim 4 wherein said exterior surface of said inner end segment and an interior surface of said cover are disposed in a predetermined, minimally spaced relation to one another.

8. The closure assembly as recited in claim 4 wherein said flow restrictor is cooperatively structured with the discharge port to establish said fluid sealing engagement by a push-force exerted on said flow restrictor, substantially independently of said sleeve.

9. A closure assembly for a medical dispenser comprising:
a tip cap including a flow restrictor and a sleeve disposed in surrounding relation to said flow restrictor,
said flow restrictor structured for a fluid sealing engagement with a discharge port of the medical dispenser,
said tip cap further including an access opening and an oppositely disposed closed end,
said closed end comprising an inner end segment formed on said flow restrictor and an outer end segment, formed on said sleeve,
said inner end segment and said outer end segment each including exterior surfaces disposed in substantially coplanar relation to one another, and
a cover fixedly connected to said sleeve in overlying, covering relation to said exterior surface of said closed end.

10. The closure assembly as recited in claim 9 wherein said cover is fixedly connected to an exterior surface of said outer end segment in spaced relation to an exterior surface of said inner end segment.

11. The closure assembly as recited in claim 9 wherein said flow restrictor is cooperatively structured with the discharge port to establish said fluid sealing engagement by a push-force exerted on said flow restrictor, substantially independently of said push-force being exerted on said sleeve.

12. The closure assembly as recited in claim 10 wherein said exterior surface of said inner end segment and an interior surface of said cover are disposed in a predetermined, minimally spaced relation to one another.

* * * * *